US008500698B2

(12) United States Patent
Kyvik et al.

(10) Patent No.: US 8,500,698 B2
(45) Date of Patent: Aug. 6, 2013

(54) CATHETER ANCHOR

(75) Inventors: Kurt Kyvik, Satellite Beach, FL (US); Scott Ryan, Ocala, FL (US); John Matson, St. Petersburg, FL (US)

(73) Assignee: Zefon International, Inc., Ocala, FL (US)

( * ) Notice: Subject to any disclaimer, the term of this patent is extended or adjusted under 35 U.S.C. 154(b) by 1062 days.

(21) Appl. No.: 11/706,634

(22) Filed: Feb. 15, 2007

(65) Prior Publication Data

US 2008/0065022 A1  Mar. 13, 2008

Related U.S. Application Data

(60) Provisional application No. 60/843,016, filed on Sep. 8, 2006.

(51) Int. Cl.
*A61M 5/32* (2006.01)

(52) U.S. Cl.
USPC ............ 604/174; 604/175; 604/179; 604/180

(58) Field of Classification Search
USPC .................................. 604/174, 175, 178–180
See application file for complete search history.

(56) References Cited

U.S. PATENT DOCUMENTS

| | | | |
|---|---|---|---|
| 3,167,072 A | 1/1965 | Stone et al. | |
| 3,826,254 A | 7/1974 | Mellor | |
| 3,834,380 A * | 9/1974 | Boyd | 604/180 |
| 4,129,128 A | 12/1978 | McFarlane | |
| 4,250,880 A | 2/1981 | Gordon | |
| 4,863,432 A | 9/1989 | Kvalo | |
| 5,037,397 A | 8/1991 | Kalt et al. | |
| 5,192,274 A | 3/1993 | Bierman | |
| 5,413,562 A | 5/1995 | Swauger | |
| 5,685,859 A * | 11/1997 | Kornerup | 604/180 |
| 6,074,368 A * | 6/2000 | Wright | 604/179 |
| 6,361,523 B1 * | 3/2002 | Bierman | 604/174 |
| 6,413,240 B1 * | 7/2002 | Bierman et al. | 604/174 |
| 6,428,516 B1 | 8/2002 | Bierman | |
| D470,936 S | 2/2003 | Bierman | |
| 6,689,104 B2 | 2/2004 | Bierman | |
| D492,411 S | 6/2004 | Bierman | |
| 6,770,055 B2 | 8/2004 | Bierman et al. | |
| 6,827,706 B2 | 12/2004 | Tollini | |
| 6,837,875 B1 | 1/2005 | Bierman | |
| D503,977 S | 4/2005 | Bierman | |
| 6,929,625 B2 | 8/2005 | Bierman | |
| 6,951,550 B2 | 10/2005 | Bierman | |
| 6,979,320 B2 | 12/2005 | Bierman | |
| 7,018,362 B2 | 3/2006 | Bierman et al. | |
| D528,206 S | 9/2006 | Bierman | |

* cited by examiner

*Primary Examiner* — Bhisma Mehta
(74) *Attorney, Agent, or Firm* — Thomas C. Saitta

(57) ABSTRACT

A catheter anchoring or securement device and system in combination with or for securing a catheter system to a patient's skin in a fixed position, the invention having a flexible anchor sheet member having an adhesive backing that adheres the flexible anchor sheet member to the patient's skin, a compressible catheter receiving pad mounted to the flexible anchor sheet member, and releasable securing strap covering the compressible catheter receiving pad, wherein the compressible catheter receiving pad is provided with a cavity or recess, the peripheral configuration of which corresponds to the footprint configuration of the catheter body member. The cavity has an axially-oriented channel extending the full width of the flexible anchor sheet member and opposing sets of retention walls defining lateral recesses, the combination of which precludes relative movement of the catheter fitting in all lateral directions.

19 Claims, 5 Drawing Sheets

CATHETER ANCHOR

This application claims the benefit of U.S. Provisional Patent Application Ser. No. 60/843,016, filed Sep. 8, 2006.

BACKGROUND OF THE INVENTION

This invention relates generally to the field of anchoring or securement systems that fix or secure a medical device, a fitting fixture or a medical delivery line, to be referred to herein generically and representationally as a catheter or catheter assembly, to a patient. More particularly, the invention relates to such systems wherein the anchoring means is adhesively secured to the patient's skin and wherein the catheter is accessible for inspection or replacement without needing to remove the anchoring means from the patient's skin.

It is often necessary to provide a medical device with an attached conduit or tubular line system for the delivery of liquid into the circulatory system of a patient, a primary example of such a system being a catheter system. Rather than removing and reinserting a new hypodermic needle every time subsequent delivery of a liquid medication is needed, it is often more efficient and more comfortable for the patient to insert a catheter needle which is then left in place on the skin, connector means being utilized to attach delivery conduits. To prevent excessive movement of the needle, the needle is typically fixed to the patient using adhesive tape or the like. In addition, the flexible catheter tubes extending from the catheter main body or hub are also secured to the patient's skin with adhesive tape members. Such a fixation method is not optimum in that over time the securing adhesive members loosen such that the tubes and catheter main body do not remain securely affixed to the patient's skin, especially if the catheter assembly passes over the wrist or other body joint. To address this problem, it is known to actually suture a catheter main body, fitting or hub directly to the patient's skin. While providing a more secure long-term method of fixation, this solution is understandably not preferred by patients and can lead to other complications such as infection.

Adhesive-based anchoring devices or systems that better secure the catheter assembly without recourse to direct suturing have been developed and are especially useful in circumstances where there is a need to inspect, adjust or substitute the catheter. These anchoring devices typically comprise a relatively rigid and bulky plastic retainer or adaptor secured to an adhesively backed flexible wrap or bandage. A portion of the catheter tube or a catheter fitting or hub is received by the retainer and secured using a hinged cover, a press fit construction or similar means. While improving on the use of adhesive tape or suturing, these devices typically use relatively hard plastic members with relatively high profiles that can be uncomfortable to the patient. Other adhesive-based anchoring devices utilize padded bodies having relatively large recesses that expose a layer of adhesive, with the catheter main body or hub being held in place by a strap or cover member. The recesses, however, do not tightly restrict movement of the catheter bodies or hubs, such that over time the catheter loosens and must be re-affixed, and at least one portion of the catheter is compressed between two sheet members which no corresponding cavity or recess. Examples of such devices are shown in U.S. Pat. No. 6,827,706 to Tollini, U.S. Pat. No. 6,428,516 to Bierman, U.S. Pat. No. 5,413,562 to Swauger, U.S. Pat. No. D492,411 to Bierman, U.S. Pat. No. D470,936 to Bierman, U.S. Pat. No. D528,206 to Bierman, U.S. Pat. No. 6,837,875 to Bierman, U.S. Pat. No. 7,018,362 to Bierman et al., U.S. Pat. No. 4,250,880 to Gordon, U.S. Pat. No. 5,037,397 to Kalt et al., U.S. Pat. No. 3,834,380 to Boyd, U.S. Pat. No. 3,826,254 to Mellor, U.S. Pat. No. 4,129,128 to McFarlane, U.S. Pat. No. 5,192,274 to Bierman, U.S. Pat. No. 4,863,432 to Kvalo, U.S. Patent No. D503,977 to Bierman, U.S. Pat. No. 6,929,625 to Bierman, U.S. Pat. No. 6,837,875 to Bierman, U.S. Pat. No. 6,689,104 to Bierman, U.S. Pat. No. 6,979,320 to Bierman, U.S. Pat. No. 6,770,055 to Bierman, and U.S. Pat. No. 6,951,550 to Bierman.

It is an object of this invention to provide a catheter anchoring device and system that improves on known such systems by providing fixed attachment to the patient in a manner that is secure, low profile, comfortable, re-positionable and easy to inspect. It is a further object to provide such a device and system wherein the catheter, and in particular the catheter body member, fitting, connector or hub, is retained and restricted in all directions, particularly in all the horizontal directions and most particularly in the axial direction, by providing a recess or cavity to receive the catheter body member that is configured to correspond with the footprint configuration of the catheter body member.

SUMMARY OF THE INVENTION

The invention is a catheter anchoring or securement device and system for securing a catheter, or more particularly the catheter body member, such as a fitting, connector, hub or the like, to a patient's skin in a fixed position, the invention in a preferred embodiment comprising a flexible anchor pad or sheet member having an adhesive backing that adheres the flexible anchor sheet member to the patient's skin, a compressible catheter receiving body or pad mounted to the exterior side of the flexible anchor sheet member, and a releasable securing strap comprising a cover or closure member covering the compressible catheter receiving pad and releasably connecting to the flexible anchor sheet member, wherein the compressible catheter receiving pad is provided with a cavity or recess, the peripheral configuration of which corresponds to the footprint configuration of the catheter body member to be secured. The compressible catheter receiving pad is substantially equal in height or thickness, or relatively close in height or thickness, to the height or thickness of the catheter body member. The cavity is structured to have retention walls that preclude relative movement of the catheter fitting in all horizontal directions, and in particular in either axial direction. The cavity comprises an axial channel extending the full width of the flexible anchor sheet member and if required a pair of lateral recesses to receive the wings of the catheter body member if present. An adhesive layer is provided in the base of the cavity to adhere to the underside of the catheter body member. With this design, the catheter body member is inserted into the cavity, the releasable closure member is brought across the catheter body member and closed, and the flexible anchoring pad is adhered to the patient's skin at the desired location. An adhesive layer may also be applied to the underside of the releasable closure member. The configuration, material of construction and thickness of the compressible catheter receiving pad secures the catheter against movement in all directions and provides a comfortable outer profile and means of securement. To inspect or replace the catheter, the closure member is opened to expose the catheter body member, which may be removed from the flexible anchor sheet member if necessary.

In a first alternative embodiment, the compressible catheter receiving pad is secured directly to the underside of the releasable closure member with the cavity exposed to the underside. As before, the catheter body member is inserted into the cavity and the closure member is releasably secured onto the flexible anchor sheet member that is adhered to the patient's skin. In another alternative embodiment, the compressible catheter receiving pad is secured to the underside of a flexible anchor sheet member such that the cavity is exposed to the underside of the flexible anchor sheet member, in a manner similar to the structure of common commercial adhesive bandages. With the catheter body member or hub inserted into the cavity, the two ends of the flexible anchor sheet member are adhered to the patient's skin and the catheter body member is itself in direct contact with the patient's skin.

DETAILED DESCRIPTION OF THE INVENTION

Figure 1:
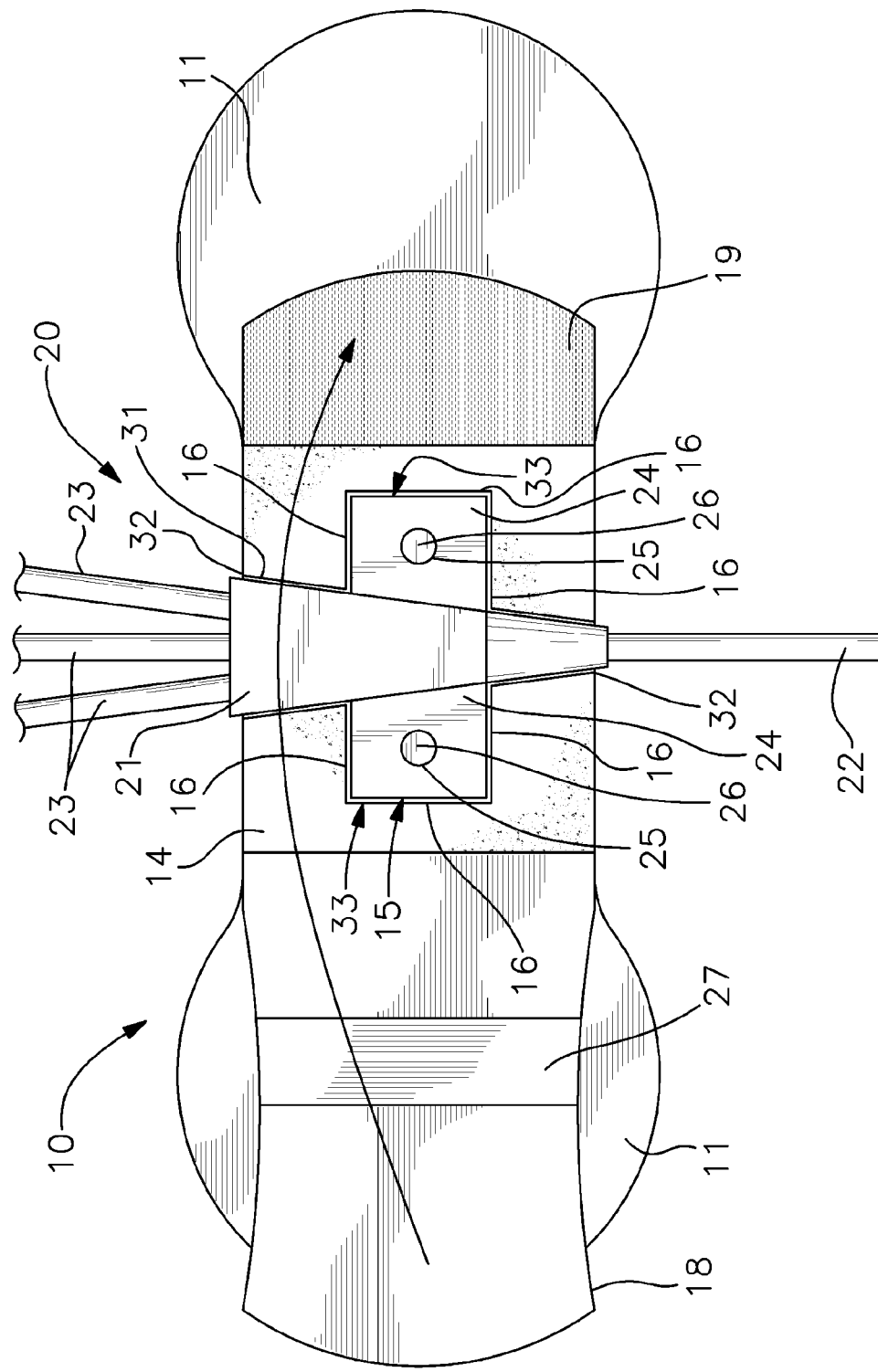
FIG. 1 is a top view of the invention, shown with the releasable closure member in the open position, thereby exposing the catheter as received within the cavity of the compressible catheter receiving pad.
Figure 2:
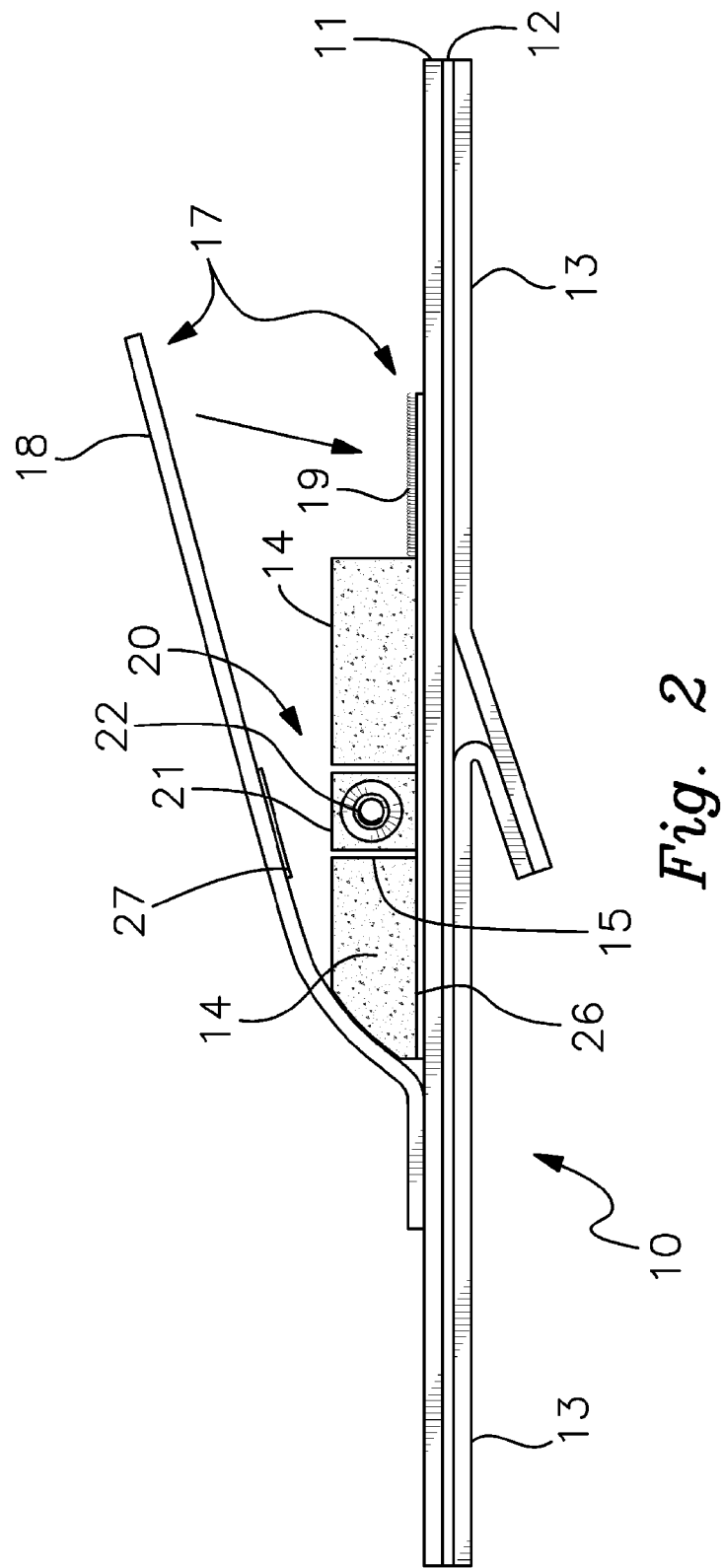
FIG. 2 is a side view of the invention, shown with the closure member in the closed position to completely secure the catheter body member against movement in any direction.

With reference to the drawings, the invention will now be described with regard for the best mode and the preferred embodiment. In a most general sense, the invention is an anchoring device or system for securing a medical device or line to the skin of a patient. In a more particular sense, the invention is an anchoring device or system in combination with or for securing a catheter to the skin of a patient, with the term catheter being taken herein to encompass a catheter system or its parts comprising conduit lines, the catheter needle and a catheter body member, this term taken herein to define a fitting, adaptor, tubing connector, hub or the like having a relatively rigid body, raised profile and a footprint exceeding that of any of the tubular conduit lines, especially in the direction transverse to the axial flow direction. As used herein, the term "horizontal" shall be taken to be the direction generally parallel to the area of the patient's skin to which the device is adhered, and the term "vertical" shall be taken to be the direction generally perpendicular to the area of the patient's skin to which the device is adhered.

A catheter 20 is a device or system for the delivery of liquids intravenously to a patient, such as for the delivery of plasma, medication, saline solutions, etc., and typically comprises a catheter body member 21, such as a fitting, adaptor, connector or hub member. The catheter body member 21 has a transverse cross-sectional configuration of greater diameter or width than the cross-sectional configuration of the feed lines 23 or main line 22, and the cross-sectional configuration is most commonly non-circular, instead typically having a more complicated polygonal configuration, such as rectangular or wedge-shaped. The catheter body member 21 receives or connects one or more feed lines 23 for delivery of the liquid into a received or connected main tube or line 22, which is in turn connected to an indwelling catheter needle that has been inserted subcutaneously into a vein or artery, or alternatively the needle is connected directly to the catheter body member 21. The generally axially elongated body member 21 further typically comprises a pair of low profile lateral wings or flanges 24, the wings 24 often being provided with suture apertures 25. Such catheter structures are well known in the art, and the particular dimensions and shape of the catheter body member 21 and wings 24 will vary. For example, the wings 24 may be relatively thin or thick compared to the thickness of the body member 21, the wings 24 may be generally rectangular, fan-shaped, etc., and the catheter body member 21 may be more or less rectilinear in cross-section, and may have varied transverse dimensions such that the body may narrow or widen along the axial direction. Regardless of the variation between catheters 20 or the various individual parts of the system to be secured, each catheter body member 21 or part thereof will have a particularly defined footprint or perimeter configuration, i.e., a defined perimeter or outline when viewed from the vertical direction.

The catheter anchoring device 10 comprises a flexible anchor pad or sheet member 11, typically formed of a relatively thin plastic or fabric material, which may be woven or punched material for increased breathability, and preferably shaped generally as a somewhat elongated strip of material in the nature of a common commercial adhesive bandage. The flexible anchor sheet member 11 is adhesive-backed, being provided with an adhesive layer 12 applied to its rear or underside. The adhesive in the adhesive layer 12 is chosen so as to be suitable for securing the flexible anchor sheet member 11 to the skin of the patient. One or more backing or release members 13 are temporarily disposed on the adhesive layer 12, the release members 13 being removed prior to use to expose the adhesive layer 12 to adhere the flexible anchor sheet member 11 to the skin. In the preferred embodiment, a compressible catheter receiving body or pad 14 is mounted onto the upper or exterior side of the flexible anchor sheet member 11, preferably by providing a catheter retention adhesive layer 26 disposed generally across the center of the upper side of the flexible anchor sheet member 11. The compressible catheter receiving pad 14 is composed of a compressible, resilient material, preferably a polymer foam or a compressible soft plastic. The height or thickness of the compressible catheter receiving pad 14 is substantially equal to the height or thickness of the catheter body member 21, or preferably slightly greater, such that there is no or relatively minimal variation in thickness when the releasable closure member 18 is in place securing the catheter body member 21. This maximizes the retentive strength of the catheter receiving pad 14 and provides for a relatively smooth or curved outer surface configuration or profile for the overall device 10 when the catheter receiving pad 14 is compressed by the releasable closure member 18.

A recess or cavity 15, open on the upper side of the catheter receiving pad 14, is provided in the catheter receiving pad 14 and is structured in a manner such that a portion of the catheter retention adhesive layer 26 is exposed within the cavity 15. The cavity 15 comprises an axially-elongated channel 31 having open ends 32, such that the channel 31 extends fully across the width of the flexible anchor sheet member 11, with the width of the open ends 32 defining generally the channel 31. The cavity 15 is constructed so as to comprise multiple sets of opposing retention walls 16, the retention walls 16 acting to preclude movement of the catheter body member 21 horizontally on the flexible anchor sheet member 11. At least one set of opposing retention walls 16 precludes movement in the direction transverse to the axial direction, at least one set of opposing retention walls 16 precludes movement in the axial direction. To this end, the material of composition of the catheter receiving pad 14 must be of sufficient density and strength to retain the catheter fitting 21 when it is pushed or pulled in any lateral or horizontal direction, and in particular in either axial direction, under the relatively low forces likely to be encountered by the patient during the wearing of the catheter anchor device 10. The cavity 15 is provided with a peripheral configuration, outline or contour that corresponds, matches and essentially mates with the footprint or perimeter configuration, as seen vertically, of the particular catheter body member 21 to be retained, such that the catheter body member 21 is snuggly retained therein with limited movement in any horizontal direction. In particular, the cavity 15 comprises an axially-oriented channel 31 having open ends 32, the channel 31 extending across the full width of the flexible anchor sheet member 11, and a pair of opposed lateral recesses 33 defined by the retention walls 16 and corresponding to the footprint configuration of the catheter body member 21 and/or the lateral wings 24 if present.

Because the configuration of the cavity 15 corresponds to the footprint of the catheter body member 21, inclusive of the wings 24, the catheter body member 21 is tightly received and retained therein. Movement of the catheter body member 21 in any lateral or horizontal direction is precluded by the combination of the retentions walls 16, the cavity channel 31 and the cavity lateral recesses 33. Because the cavity channel 31 has open ends 32, no portion of the catheter body member 21 or tubes 22 and 23 are compressed between sheet members lacking a corresponding recess to accommodate that portion of the catheter body member 21 or tubes 22 or 23. The exposed adhesive layer 26 within the cavity 15 further secures the catheter body member 21 in fixed position to preclude any horizontal movement.

The catheter body member 21 is further retained within the cavity 15 by a releasable securing strap 17 such that the catheter body member 21 and cavity 15 can be accessed when desired. A preferred releasable securing strap 17 comprises a hook-and-loop fastener assembly, wherein a hook layer 19 is mounted onto the upper side of the flexible anchor sheet member 11 on at least one side of the catheter receiving pad 14, and an extended cover or closure member 18, either comprising the loops or nap of the fastener or having them attached thereto, is secured to the upper side of the flexible anchor sheet member 11 on the opposite side of the catheter receiving pad 14 from the hook layer 19. The cover member 18 is pulled across the catheter body member 21 and catheter receiving pad 14, and then joined to the hook layer 19 to temporarily retain the catheter body member 21 and preclude any movement in the vertical direction. An additional adhesive layer or strip 27 may be applied to the underside of the cover member 18 at a position of contact with the catheter body member 21. Inspection or removal of the catheter body member 21 is readily accomplished by separating one end of the cover member from the flexible anchor sheet member 11 to expose the catheter receiving pad 14. Because the catheter receiving pad 14 is compressible, when the cover member 18 is pulled into place, the external profile or contour presented by the device 10 is relatively smooth with no pronounced edges or corners that may more easily snag upon other objects. The compression of the catheter receiving pad 14 by the cover member 18 also increases the structural rigidity of the catheter receiving pad 14 to better secure the catheter body member 21 against movement in all horizontal directions.

Figure 3:
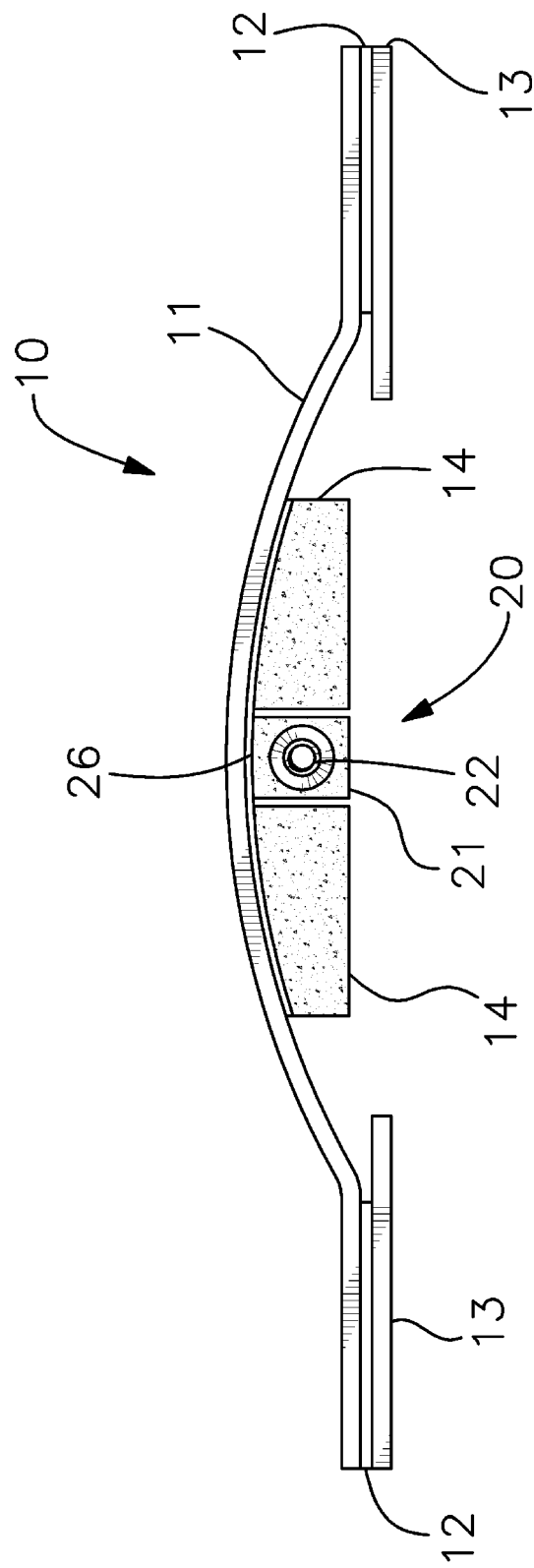
FIG. 3 is a side view of an alternative embodiment for the invention, wherein the compressible catheter receiving pad is affixed to the underside of the flexible anchor sheet member.

In an alternative embodiment as shown in FIG. 3, the catheter anchor device 10 comprises a flexible anchor sheet member 11 having an adhesive layer 12 disposed on its underside at least adjacent each end, the adhesive layer 12 being covered by removable release members 13. The compressible catheter receiving pad 14 is mounted on the underside of the flexible anchor sheet member 11 with the cavity 15 open to the underside of the catheter receiving pad 14. As before, a catheter retention adhesive layer 26 is preferably provided on the underside of the flexible anchor sheet member 11 so as to be exposed within the cavity 15. With this design, the catheter body member 21 is inserted into the cavity 15 on underside of the catheter receiving pad 14 and held against the patient's skin when the flexible anchor sheet member 11 is adhered to the patient.

Figure 4:
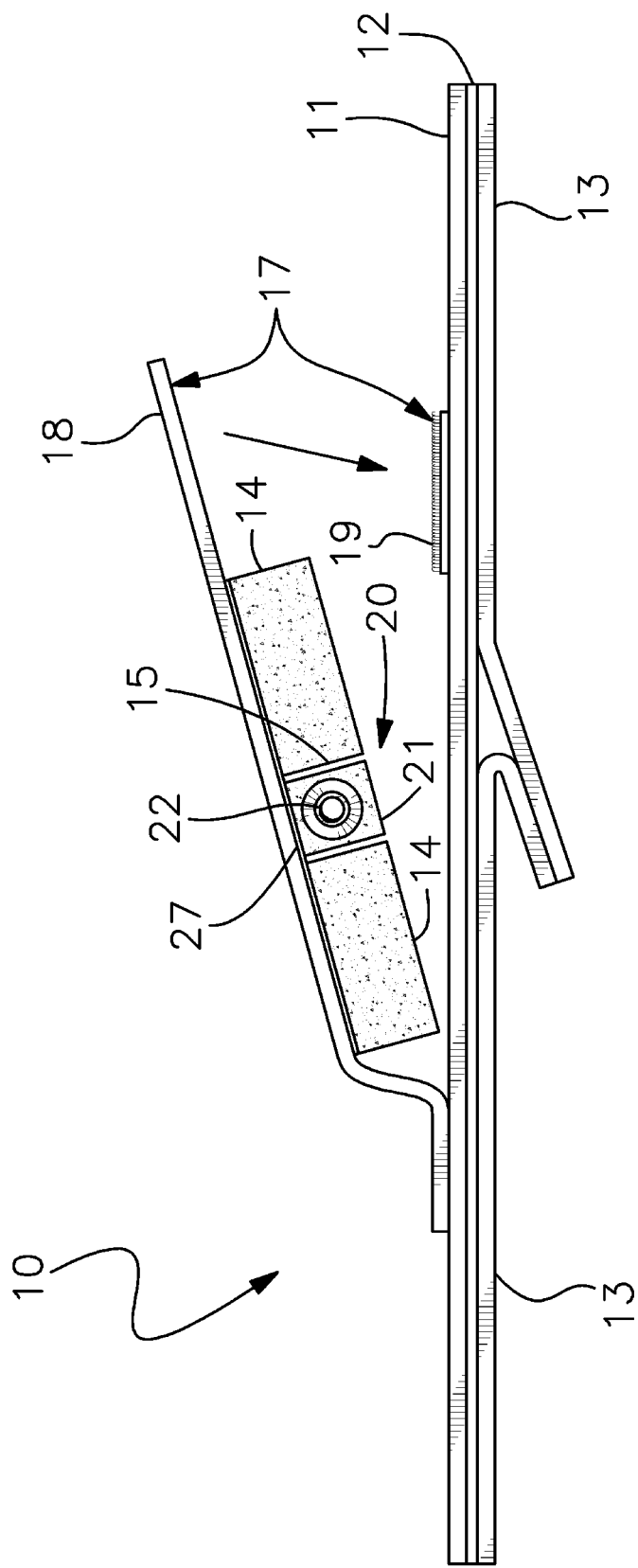
FIG. 4 is a side view of another alternative embodiment of the invention, wherein the compressible catheter receiving pad is affixed to the underside of the releasable closure member.
Figure 5:
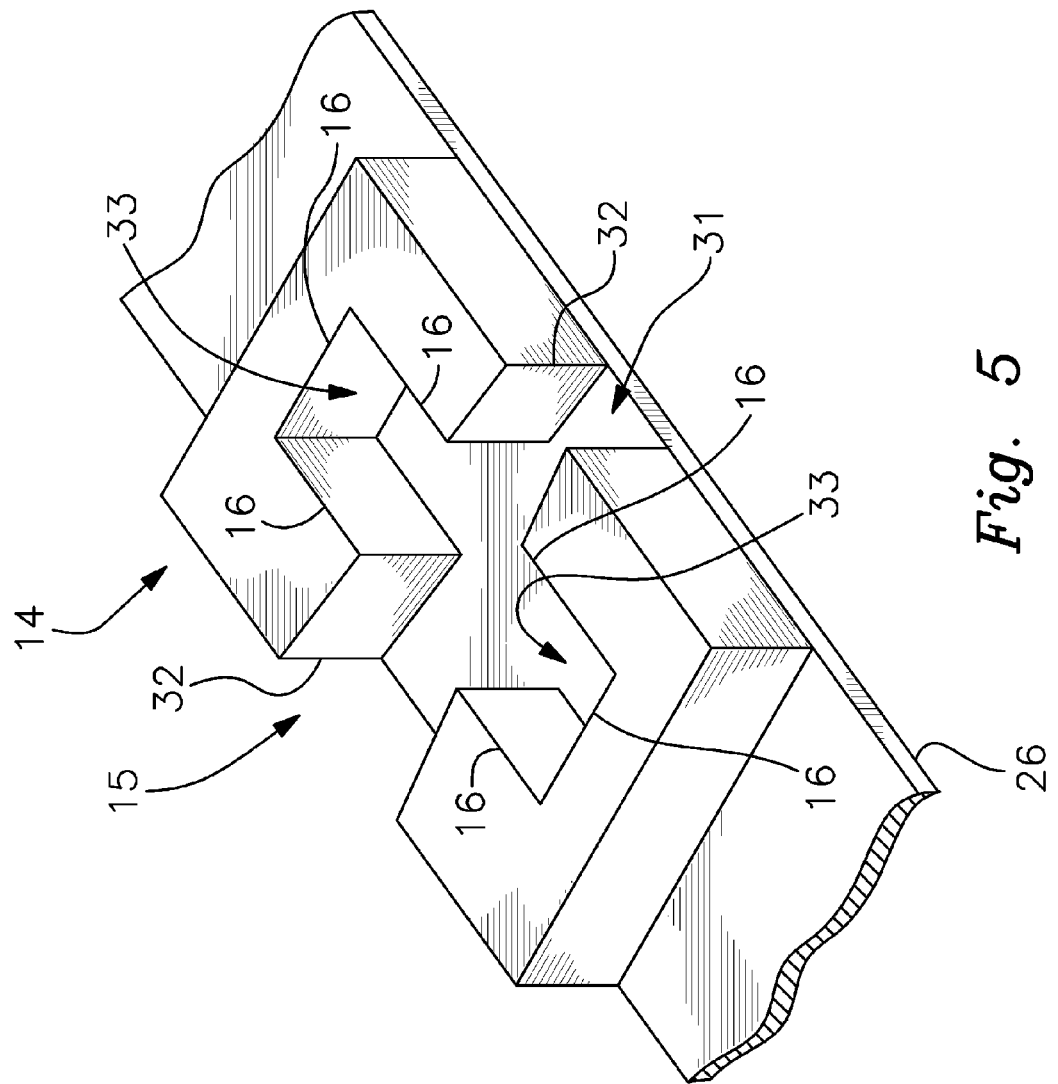
FIG. 5 is a perspective view of the compressible catheter receiving pad, showing the cavity comprising the channel and lateral recesses.

In another alternative embodiment more similar in structure to the main embodiment and shown in FIG. 4, the catheter receiving pad 14 is secured to the underside of the releasable securing strap 17 such that the open side of the cavity 15 faces down, again preferably by an adhesive layer 27 which is exposed within the cavity 15 as before. In this embodiment, the catheter body member 21 is first inserted into the cavity 15, the releasable securing strap 17 is then affixed to the flexible anchor sheet member 11, and the flexible anchor sheet member 11 is then adhered to the patient's skin.

It is understood that equivalents and substitutions to certain elements and structures set forth above may be obvious to those skilled in the art, and therefore the true scope and definition of the invention is to be as set forth in the following claims.

We claim:

1. In combination, a catheter anchoring device and catheter body member;

said catheter body member having a footprint configuration, a thickness and defining an axial direction corresponding to the direction of flow through said catheter body member, said catheter body member receiving one or more catheter tubes;

said catheter anchoring device comprising an adhesive-backed flexible anchor sheet member, a compressible catheter receiving pad mounted onto said flexible anchor sheet member, said compressible catheter receiving pad being composed of a polymer foam material, a cavity disposed in said compressible catheter receiving pad, and a releasable securing strap retaining said catheter body member within said cavity of said compressible catheter receiving pad;

said cavity comprising an elongated channel with open ends, said channel extending fully across said flexible anchor sheet member, said cavity further comprising sets of opposing retention walls, said cavity having a peripheral configuration matching and mating with said footprint configuration of said catheter body member; and whereby said catheter body member is precluded from horizontal movement in all directions by said sets of opposing retention walls.

2. The combination of claim 1, further comprising an adhesive layer disposed within said cavity.

3. The combination of claim 1, said compressible catheter receiving pad having a thickness substantially equal to the thickness of said catheter body member.

4. The combination of claim 1, wherein one of said sets of opposing retention walls precludes movement of said catheter body member in the direction transverse to the axial direction and another of said sets of opposing retention walls precludes movement of said catheter body member in the axial direction.

5. The combination of claim 1, wherein said releasable securing strap comprises a hook-and-loop fastener assembly.

6. The combination of claim 1, further comprising an adhesive layer disposed on said releasable securing strap, said adhesive layer contacting said catheter body member.

7. The combination of claim 1, wherein said releasable securing strap compresses said compressible catheter receiving pad to define a smooth exterior profile across said catheter anchoring device.

8. In combination, a catheter anchoring device and catheter body member;
- said catheter body member having a footprint configuration, a thickness and defining an axial direction corresponding to the direction of flow through said catheter body member, said catheter body member receiving one or more catheter tubes;
- said catheter anchoring device comprising an adhesive-backed flexible anchor sheet member, a releasable securing strap mounted onto said flexible anchor sheet member, a compressible catheter receiving pad mounted onto said releasable securing strap, said compressible catheter receiving pad being composed of a polymer foam material, and a cavity disposed in said compressible catheter receiving pad, said releasable securing strap retaining said catheter body member within said cavity of said compressible catheter receiving pad and against said flexible anchor sheet member;
- said cavity comprising an elongated channel with open ends, said channel extending fully across said flexible anchor sheet member, said cavity further comprising sets of opposing retention walls, said cavity having a peripheral configuration matching and mating with said footprint configuration of said catheter body member; and
- whereby said catheter body member is precluded from horizontal movement in all directions by said sets of opposing retention walls.

9. The combination of claim 8, further comprising an adhesive layer disposed within said cavity.

10. The combination of claim 8, said compressible catheter receiving pad having a thickness substantially equal to the thickness of said catheter body member.

11. The combination of claim 8, wherein one of said sets of opposing retention walls precludes movement of said catheter body member in the direction transverse to the axial direction and another of said sets of opposing retention walls precludes movement of said catheter body member in the axial direction.

12. The combination of claim 8, wherein said releasable securing strap comprises a hook-and-loop fastener assembly.

13. The combination of claim 8, further comprising an adhesive layer disposed on said flexible anchor sheet member, said adhesive layer contacting said catheter body member.

14. The combination of claim 8, wherein said releasable securing strap compresses said compressible catheter receiving pad to define a smooth exterior profile across said catheter anchoring device.

15. In combination, a catheter anchoring device and catheter body member;
- said catheter body member having a footprint configuration, a thickness and defining an axial direction corresponding to the direction of flow through said catheter body member, said catheter body member receiving one or more catheter tubes;
- said catheter anchoring device comprising an adhesive-backed flexible anchor sheet member, a compressible catheter receiving pad mounted onto the underside of said flexible anchor sheet member, said compressible catheter receiving pad being composed of a polymer foam material, and a cavity disposed in said compressible catheter receiving pad;
- said cavity comprising an elongated channel with open ends, said channel extending fully across said flexible anchor sheet member, said cavity further comprising sets of opposing retention walls, said cavity having a peripheral configuration matching and mating with said footprint configuration of said catheter body member; and
- whereby said catheter body member is precluded from horizontal movement in all directions by said sets of opposing retention walls.

16. The combination of claim 15, further comprising an adhesive layer disposed within said cavity.

17. The combination of claim 15, said compressible catheter receiving pad having a thickness substantially equal to the thickness of said catheter body member.

18. The combination of claim 15, wherein one of said sets of opposing retention walls precludes movement of said catheter body member in the direction transverse to the axial direction and another of said sets of opposing retention walls precludes movement of said catheter body member in the axial direction.

19. The combination of claim 15, wherein said flexible anchor sheet member compresses said compressible catheter receiving pad to define a smooth exterior profile across said catheter anchoring device.

* * * * *